United States Patent
Hohman

(10) Patent No.: US 9,939,391 B1
(45) Date of Patent: Apr. 10, 2018

(54) INSPECTION METHOD USING A FILM OVERLAY

(71) Applicant: Bell Helicopter Textron Inc., Fort Worth, TX (US)

(72) Inventor: Edward A. Hohman, Mansfield, TX (US)

(73) Assignee: Bell Helicopter Textron Inc., Fort Worth, TX (US)

( * ) Notice: Subject to any disclaimer, the term of this patent is extended or adjusted under 35 U.S.C. 154(b) by 5 days.

(21) Appl. No.: 15/380,408

(22) Filed: Dec. 15, 2016

(51) Int. Cl.
*G01B 11/00* (2006.01)
*G01N 21/956* (2006.01)
*G01N 21/88* (2006.01)

(52) U.S. Cl.
CPC ... *G01N 21/95607* (2013.01); *G01N 21/8806* (2013.01); *G01N 21/8851* (2013.01)

(58) Field of Classification Search
CPC ......... G01N 21/95607; G01N 21/8806; G01N 21/8851
USPC .................................. 356/399–401
See application file for complete search history.

(56) References Cited

U.S. PATENT DOCUMENTS

| | | | |
|---|---|---|---|
| 6,296,378 B1 | 10/2001 | Doyen | |
| 6,484,583 B1 | 11/2002 | Chennell et al. | |
| 6,735,575 B1 | 5/2004 | Kara | |
| 7,614,304 B2 | 11/2009 | Gunasekaran et al. | |
| 8,004,689 B2 | 8/2011 | Monchalin et al. | |
| 9,110,442 B1* | 8/2015 | Raiford | G03H 1/0011 |
| 2006/0103853 A1* | 5/2006 | Palmateer | B64F 5/60 356/601 |
| 2012/0286094 A1 | 11/2012 | Petsche et al. | |
| 2016/0061779 A1 | 3/2016 | Barry et al. | |
| 2017/0068877 A1* | 3/2017 | Mosteller | G06K 19/07722 |

FOREIGN PATENT DOCUMENTS

| | | |
|---|---|---|
| GB | 2021280 A | 11/1979 |
| WO | 2007005687 A1 | 1/2007 |

* cited by examiner

*Primary Examiner* — Hina F Ayub
(74) *Attorney, Agent, or Firm* — Timmer Law Group, PLLC

(57) ABSTRACT

A method of inspecting a component using a film overlay including providing the component, the component having a first surface, a core, and a second surface; positioning a film overlay having a reference indicia and a structural indicia on the first surface of the component; aligning the reference indicia on the film overlay with a reference feature on the component; positioning a testing probe on a top surface of the film overlay so the probe is aligned with the structural indicia; and transmitting a signal from the probe through the film overlay, the first surface, the core, and the second surface.

19 Claims, 12 Drawing Sheets

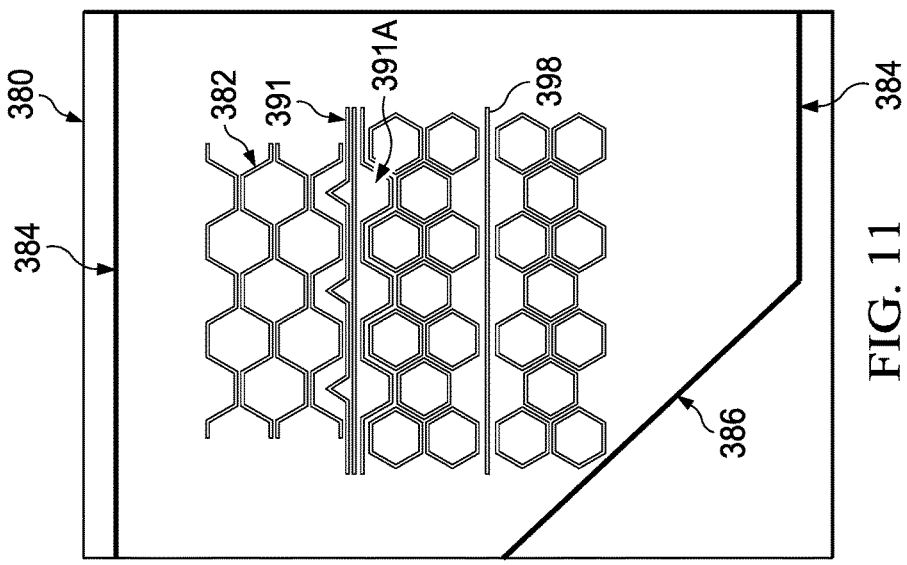
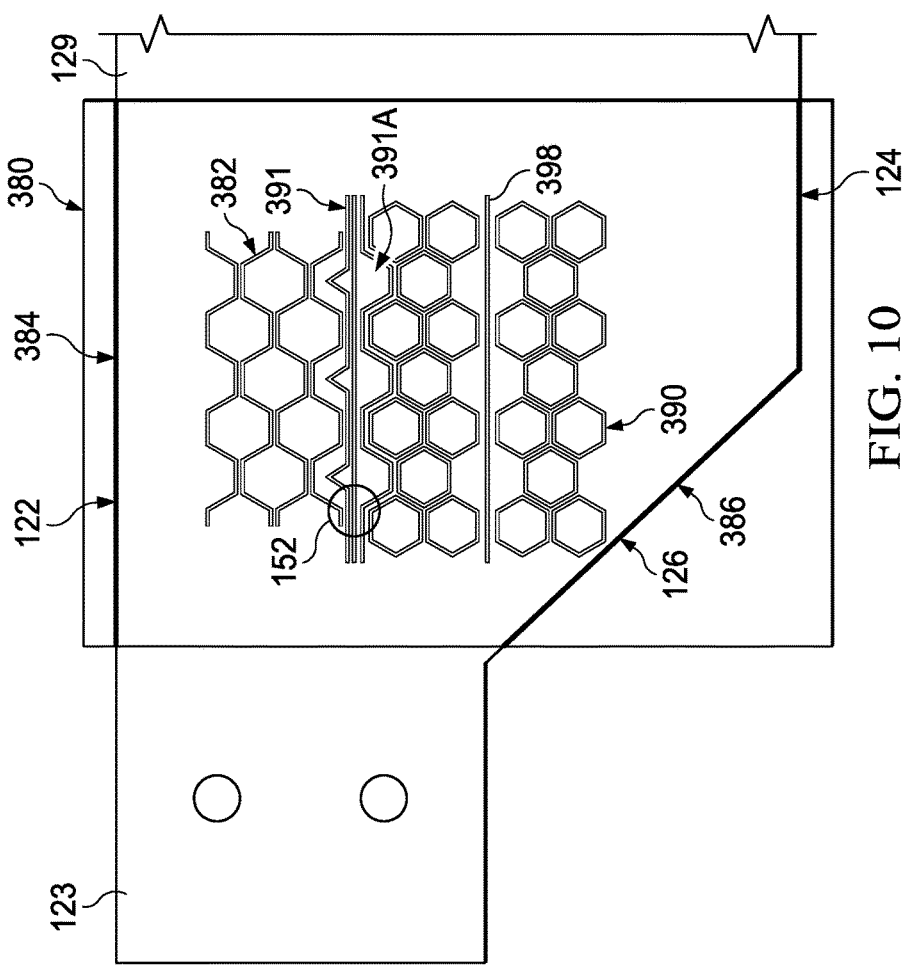

INSPECTION METHOD USING A FILM OVERLAY

BACKGROUND

Technical Field

The present disclosure relates to inspection of a part, e.g. composite or other internally reinforced components for an aircraft.

Description of Related Art

In many industries, components are inspected for defects in a field environment. Inspection methods and techniques may be employed to determine the integrity of a part or a component. Knowing the geometric details of a part along with hidden details such as multiple co-bonded materials, adhesive bondlines, and sandwiched details is critical to a successful inspection. Inspection from the outside surface of a part may be the most suitable option and the inspector may not have intimate knowledge of the geometric features or substructures associated with that part, which makes inspection difficult to perform reliably and may not provide enough fidelity to detect small defects.

Non-destructive testing methods such as ultrasonic testing, bond testing, or eddy current testing involve positioning a probe over a general area on the outer surface of the component. As the probe is placed over the general area, the inspector must identify certain hidden features without any detailed references. There is a need for a non-destructive testing method involving an overlay that can be used to identify internal core structure details.

SUMMARY

In a first aspect, there is a method of inspecting a component including providing the component, the component having a first surface, a core, and a second surface; positioning a film overlay having a reference indicia and a structural indicia on the first surface of the component; aligning the reference indicia on the film overlay with a reference feature on the component; positioning a testing probe on a top surface of the film overlay so the probe is aligned with the structural indicia; and transmitting a signal from the probe through the film overlay, the first surface, the core, and the second surface.

In an embodiment, the method includes receiving a response signal by the probe; and inspecting the component based on the response signal.

In yet another embodiment, the reference indicia visually conveys information about the location of a reference feature on the component to identify the position of the film overlay on the component.

In an embodiment, the reference indicia is an image representing a reference feature selected from the group consisting of: an exterior feature, an internal structural feature, and an internal non-structural feature.

In still another embodiment, the structural indicia visually conveys information about the location of a structural feature within the component.

In yet another embodiment, the structural indicia is at least one image representing a structural feature selected from the group consisting of a first surface, a core, a second surface, a skin, multi-layer material stiffener, a composite layer, changing ply thickness, a co-bonded stiffener, a secondary adhesive bonded stiffener, a material layup, a hex-shaped honeycomb core, a cellular based core, a composite with unidirectional materials, a composite with bias materials, a composite with tri-axial materials, a material, a fiber direction, a ribbon direction, a ply thickness, a ply buildup, a ply drop-off, a mix of fibers, a tow angle, a bundle angle, a tow-size, a slit width, a tow separation, a bundle separation, a helical cell, an encapsulated material, internal variable members, an internal bracing member, a plurality of materials sandwiched together, a carbon epoxy sheet, a fiberglass sheet, a primary structural member, a secondary structural member, a substructure, a bondline, a septum, a web stiffener location indicating the location of an I-beam stiffener, and, a partially corrugated, septum.

In an embodiment, the film overlay is a polyimide film.

In a second aspect, the film overlay for inspecting a component including a transparent film sheet, a reference indicia positioned on the sheet, and a structural indicia positioned on the sheet. The reference indicia visually conveys information about the location of a reference feature on the component to identify the position of the film overlay on the component. The structural indicia visually conveys information about the location of a structural feature within the component.

In an example, the film is a polyimide film.

In another example, the reference indicia is an image representing a reference feature selected from the group consisting of: an exterior feature, an internal structural feature, and an internal non-structural feature.

In yet another example, the structural indicia is at least one image representing a structural feature selected from the group consisting of a first surface, a core, a second surface, a skin, multi-layer material stiffener, a composite layer, changing ply thickness, a co-bonded stiffener, a secondary adhesive bonded, stiffener, a material layup, a hex-shaped honeycomb core, a cellular based core, a composite with unidirectional materials, a composite with bias materials, a composite with tri-axial materials, a material, a fiber direction, a ribbon direction, a ply thickness, a ply buildup, a ply drop-off, a mix of fibers, a tow angle, a bundle angle, a tow-size, a slit width, a tow separation, a bundle separation, a helical cell, an encapsulated material, internal variable members, an internal bracing member, a plurality of materials sandwiched together, a carbon epoxy sheet, a fiberglass sheet, a primary structural member, a secondary structural member, a substructure, a bondline, a septum, a web stiffener location indicating the location of an I-beam stiffener, and a partially corrugated septum.

In still another embodiment, the structural indicia is at least one image representing the absence of the structural feature.

In an embodiment, the structural indicia is at least one image representing an individual structural feature.

In one embodiment, the structural indicia is at least one image representing a plurality of structural features.

In an embodiment, the structural indicia is at least one image representing a physical property of the structural feature.

In yet another embodiment, the structural indicia is selected from the group consisting of: maintenance instructions, service instructions, and installation instructions.

In a third aspect, there is provided a method of inspecting a component including providing the component, the component having a first surface, a core, and a second surface; generating a film overlay for use with a projector, the film overlay having a reference indicia and a structural indicia that provides an image of the reference indicia and structural indicia on the component; and configuring a projector with the film overlay so that a reference feature of the component is aligned with an image of the reference indicia and the image of the structural indicia conveys information about the location of a structural feature within the component.

In an embodiment, the method includes positioning a testing probe on a top surface of component so the probe is aligned with the image of the structural indicia; and transmitting a signal from the probe through the first surface, the core, and the second surface.

In an embodiment, the method includes receiving a response signal by the probe; and inspecting the component based on the response signal.

Other aspects, features, and advantages will become apparent from the following detailed description when taken in conjunction with the accompanying drawings, which are a part of this disclosure and which illustrate, by way of example, principles of the inventions disclosed.

DESCRIPTION OF THE DRAWINGS

The novel features believed characteristic of the embodiments of the present disclosure are set forth in the appended claims. However, the embodiments themselves, as well as a preferred mode of use, and further objectives and advantages thereof, will best be understood by reference to the following detailed description when read in conjunction with the accompanying drawings, wherein:

FIG. 10 is a top view of the root section of the rotor blade in FIG. 7 with a film overlay positioned on a top surface, according to one example embodiment;

FIG. 11 is a top view of the film overlay in FIG. 10, according to one example embodiment;

DESCRIPTION OF THE PREFERRED EMBODIMENT

Illustrative embodiments of the apparatus and method are described below. In the interest of clarity, all features of an actual implementation may not be described in this specification. It will of course be appreciated that in the development of any such actual embodiment, numerous implementation-specific decisions must be made to achieve the developers specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

In the specification, reference may be made to the spatial relationships between various components and to the spatial orientation of various aspects of components as the devices are depicted in the attached drawings. However, as will be recognized by those skilled in the art after a complete reading of the present application, the devices, members, apparatuses, etc. described herein may be positioned in any desired orientation. Thus, the use of terms such as "above," "below," "upper," "lower," or other like terms to describe a spatial relationship between various components or to describe the spatial orientation of aspects of such components should be understood to describe a relative relationship between the components or a spatial orientation of aspects of such components, respectively, as the device described herein may be oriented in any desired direction. The use of the term "indicia" includes one or more identifying marks or indications signifying features that can be used by the inspector to inspect a component.

Figure 1:
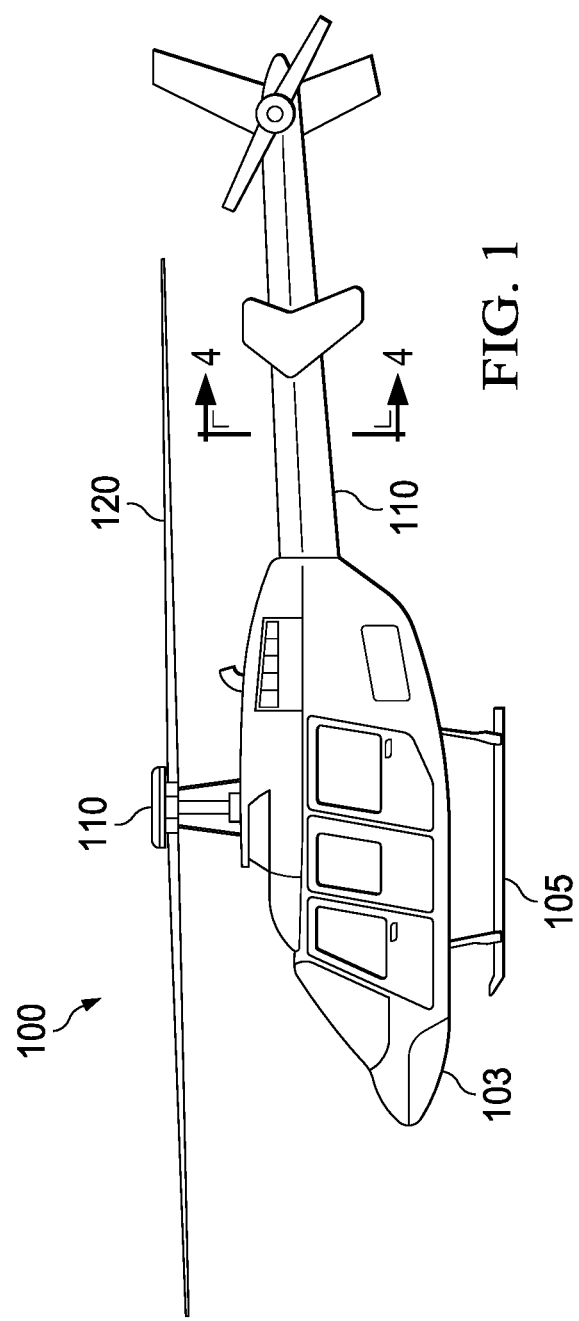
FIG. 1 is a perspective view of an aircraft, according to one example embodiment.

Referring to FIG. 1, a rotorcraft 100 is illustrated. Rotorcraft 100 includes a rotor system 110, a plurality of rotor blades 120, fuselage 103, a landing gear 105, and a tail member 110. It should be appreciated that rotorcraft 100 is merely illustrative of a variety of aircraft that can implement the methods and systems disclosed herein.

Further, methods and systems disclosed herein can be implemented to inspect and test components for a variety of aircraft structural implementations, for example, and not limitation, propellers; rotor blades; flight controls, such as, rudders, ailerons, flaps, elevators, and spoilers; and wings. Even further the methods and systems disclosed herein can be implemented to inspect and test components in non-aircraft implementations, for example, and not limitation, space, petroleum, watercraft, wind power, automotive, underwater, vehicle, and sporting components.

Figure 2:
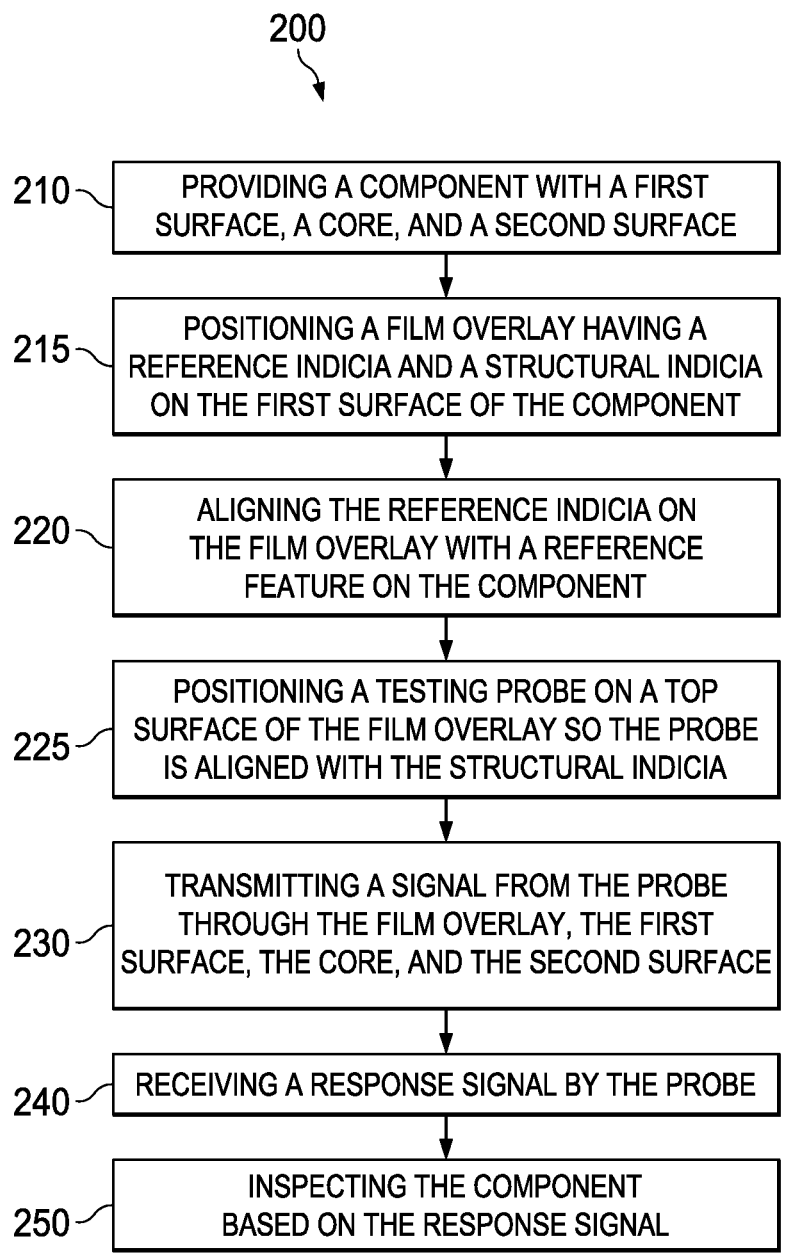
FIG. 2 shows a flowchart of an example inspection process for a component, according to one example embodiment.

FIG. 2 shows a flowchart of an exemplary embodiment of a non-destructive inspection method 200 that can be used on components of the aircraft 100. A component is provided that includes a first surface and a second surface 210. In some embodiments, a core is disposed between the first and second surface. The core can include at least one internal structure feature. In some embodiments, the core can be at least one of the following: a composite core, a reinforced core, layered core, a bonded reinforcement, and a structural core. The core can be at least one of the following internal structural features: a first surface, a core, a second surface, a skin, multi-layer material stiffener, a composite layer, changing ply thickness, a co-bonded stiffener, a secondary adhesive bonded stiffener, a material layup, a hex-shaped honeycomb core, a cellular based core, a composite with unidirectional materials, a composite with bias materials, a composite with tri-axial materials, a material, a fiber direction, a ribbon direction, a ply thickness, a ply buildup, a ply drop-off, a mix of fibers, a tow angle, a bundle angle, a tow-size, a slit width, a tow separation, a bundle separation, a helical cell, an encapsulated material, internal variable members, an internal bracing member, a plurality of materials sandwiched together, a carbon epoxy sheet, a fiberglass sheet, a primary structural member, a secondary structural member, a substructure, a bondline, a septum, a web stiffener location indicating the location of an I-beam stiffener, and a partially corrugated septum.

A film overlay is positioned on the first surface of the component 215. The film overlay includes a reference indicia and a structural indicia. The film overlay is then positioned such that the reference indicia on the film overlay is aligned with a reference feature on the component 220.

A testing probe is positioned on a top surface of the film overlay so that the probe is aligned on the structural indicia 225. A signal is transmitted from a signal generator connected to a computing device to the probe. The probe transmits a signal through the first surface, the core, and the second surface 230. The probe can receive a response signal from the second surface or other exterior surface of the component 240. The inspecting of the component based on the response signal 250 can be performed on a computing device connected to the probe or by an inspector monitoring the response signal 250. In one embodiment, the inspection method 200 is at least one of the following: an ultrasonic test, an eddy current test, a bond test using pitch-catch technique, a mechanical impedance analysis technique, a resonance technique, a tap hammer technique (manual or digital), and thermography.

Figure 3:
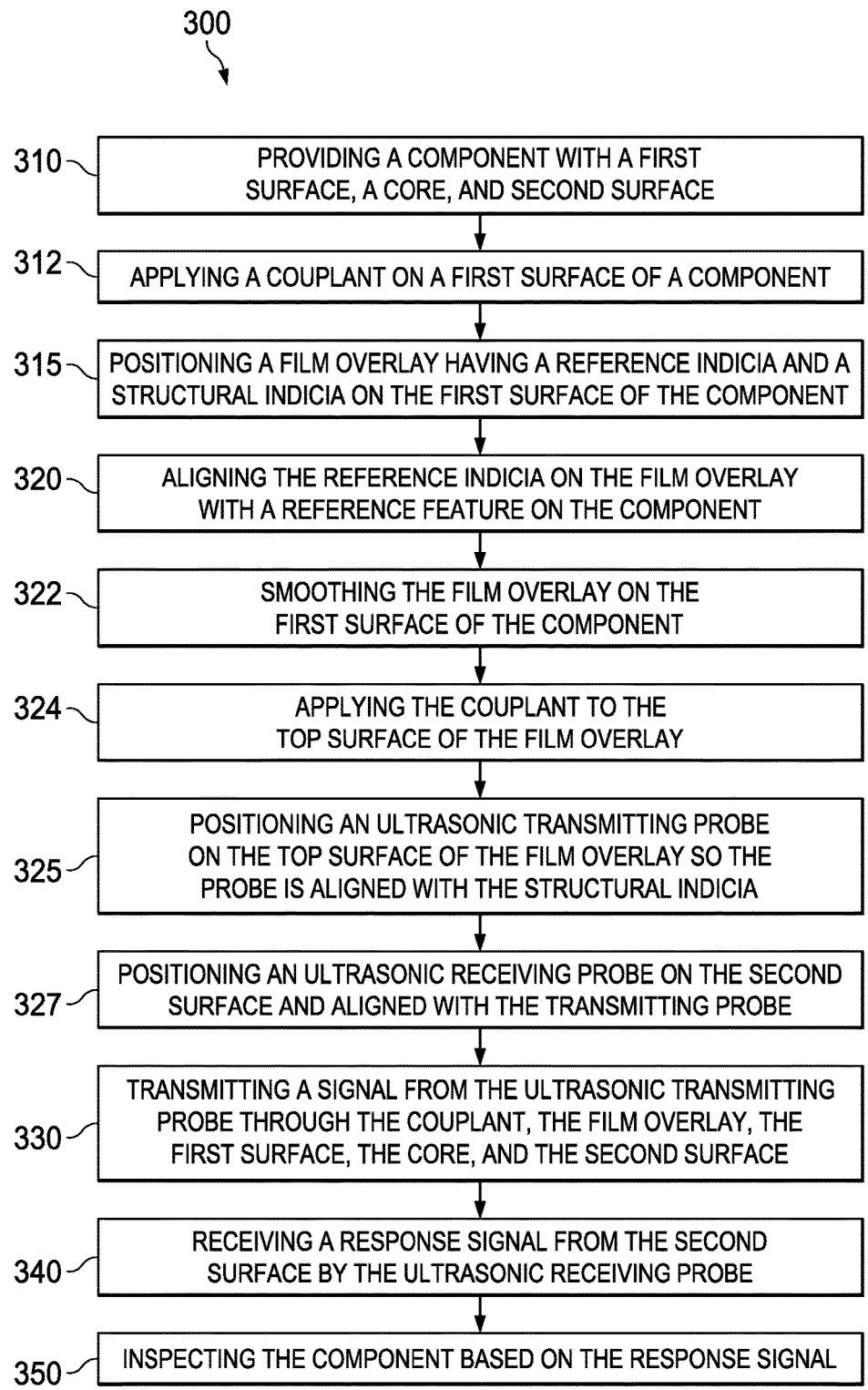
FIG. 3 shows a flowchart of an example inspection process for a component, according to one example embodiment.

Another exemplary embodiment of a non-destructive inspection method 300 is shown in FIG. 3 involving a through-transmission ultrasonic inspection system for components of aircraft 100. Certain steps of the method 300 are as described above in connection with the inspection method 200. Those steps bear similar reference characters, but with a leading '3' rather than a leading '2'. A couplant can be applied to a first surface of the component to assist in transmission of the ultrasonic signal in step 312. In one embodiment, the couplant provides a thin film on the first surface, which has a surface tension to hold the film overlay thereon. Once the reference indicia on the film overlay is aligned with a reference feature on the component, the film overlay can be smoothed on the first surface of the component 322 to remove any air bubbles that may impede the ultrasonic signal transmission. The couplant can be applied to the top surface of the film overlay 324 to assist the ultrasonic transmission from the probe, to the film overlay, and ultimately through the component. In one embodiment, the couplant is water or other liquid that facilitates the transmission of ultrasonic signals from the probe to the component.

The method 300 includes an ultrasonic transmitting probe and an ultrasonic receiving probe. The ultrasonic transmitting probe is positioned adjacent to a top surface of the film overlay so the probe is aligned with the structural indicia in step 325. The ultrasonic receiving probe is positioned adjacent to the second surface and aligned with the transmitting probe in step 327. The transmitting probe sends an ultrasound signal through the couplant, the film overlay, the first surface, the core, and the second surface 330. The receiving probe receives the ultrasonic response signal 340, which is the amount of sound that has reached the second surface adjacent to the receiving probe. Imperfections or other conditions in the space between the first surface and the second surface reduce the amount of sound transmitted, revealing their presence during the inspecting step 350.

The methods disclosed herein can be used to inspect aircraft 100 components during the manufacturing process, as part of a maintenance program, and out in the field when imperfections or damage to the component is suspected. The exemplary methods 200 and 300 are shown herein with respect to a tail boom 160 in FIGS. 4 and 5 and the rotor blade 120 in FIGS. 6-11. However, the methods disclosed herein can be implemented to inspect and test components for a variety of aircraft structural implementations, for example, and not limitation, propellers; flight controls, such as, rudders, ailerons, flaps, elevators, and spoilers; and wings. Even further the methods and systems disclosed herein can be implemented to inspect and test components in non-aircraft implementations, for example, and not limitation, space, petroleum, watercraft, wind power, automotive, underwater, vehicle, and sporting components.

The tail member 110 of aircraft 100 includes a tail boom 160. The tail boom 160 has first side wall 162, a top wall 164, a second side wall 166, and a bottom wall 168. Each of the walls includes an exterior surface 162a, 164a, 166a, and 168a; and an interior surface 162b, 164b, 166b and 168b, respectively. The exterior surfaces of 162a, 164a, 166a, and 168a can be at least one skin or a plurality of skins that wrap around the tail boom 160 as the outermost laminate or metallic structure. In one embodiment, stiffeners, ply buildup, longerons, and ribs can be included as internal bracing members 170 to reinforce the skin.

The core of first side surface 162b, the second side surface 166b, and bottom surface 168b includes a plurality of internal bracing members or stiffeners 170 as internal structural features. The interior surfaces of the second side wall 166b and the bottom wall 168b are shown broken away to illustrate the core having internal bracing members 170. The internal bracing members 170 are normally covered by the interior surfaces 166b and 168b.

The internal bracing members 170 are part of a core that can contribute to the aerodynamic functionality of the tail boom 160. The internal structures 170 can include a plurality of materials sandwiched together; for example, but not limitation, carbon epoxy sheets and fiberglass sheets.

Figure 4A:
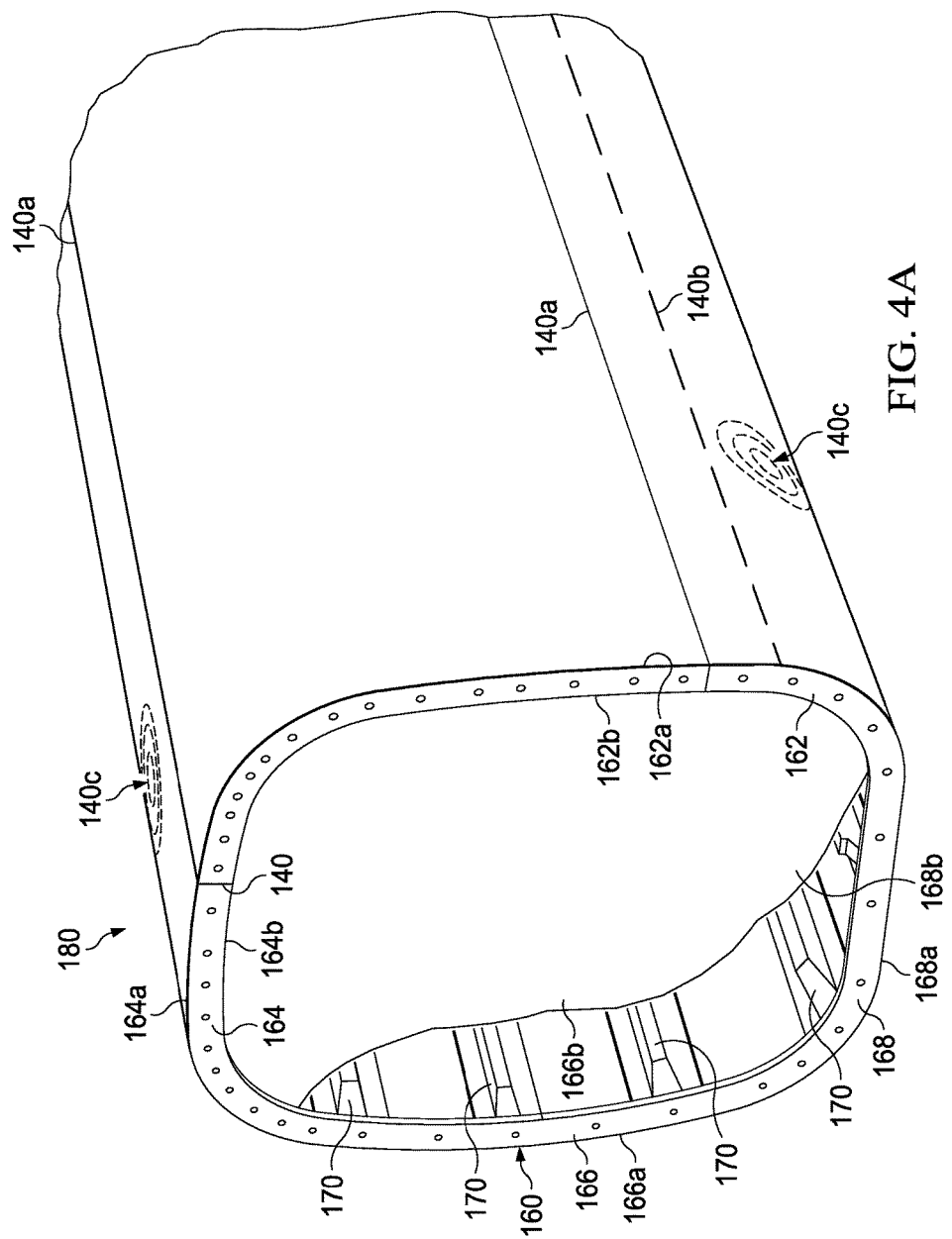
FIG. 4A is a perspective view of a tail boom component prior to testing, according to one example embodiment.
Figure 4B:
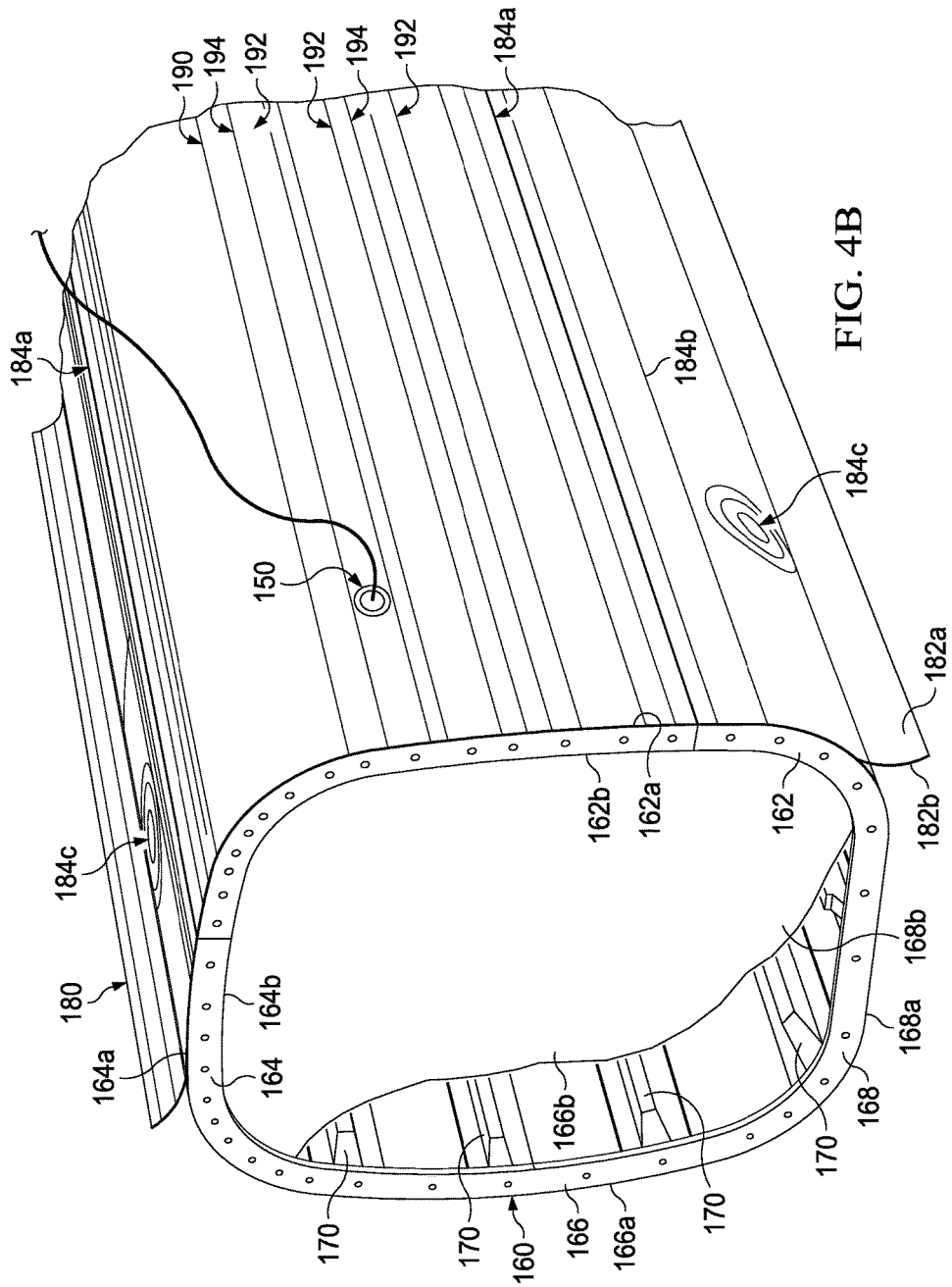
FIG. 4B is a perspective view of a tail boom component with a film overlay, according to one example embodiment.
Figure 4C:
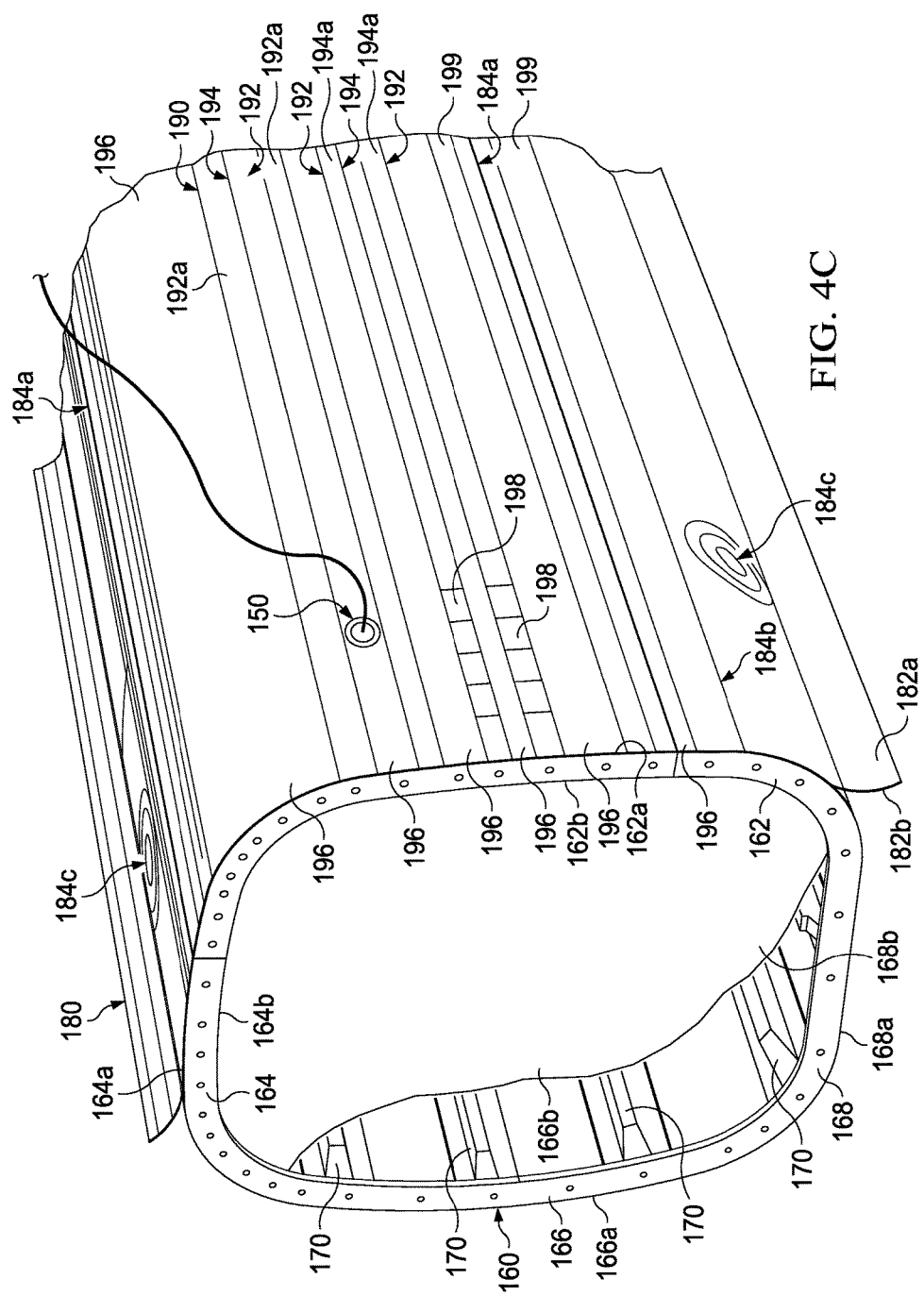
FIG. 4C is a perspective view of a tail boom component with a film overlay, according to one example embodiment.
Figure 5:
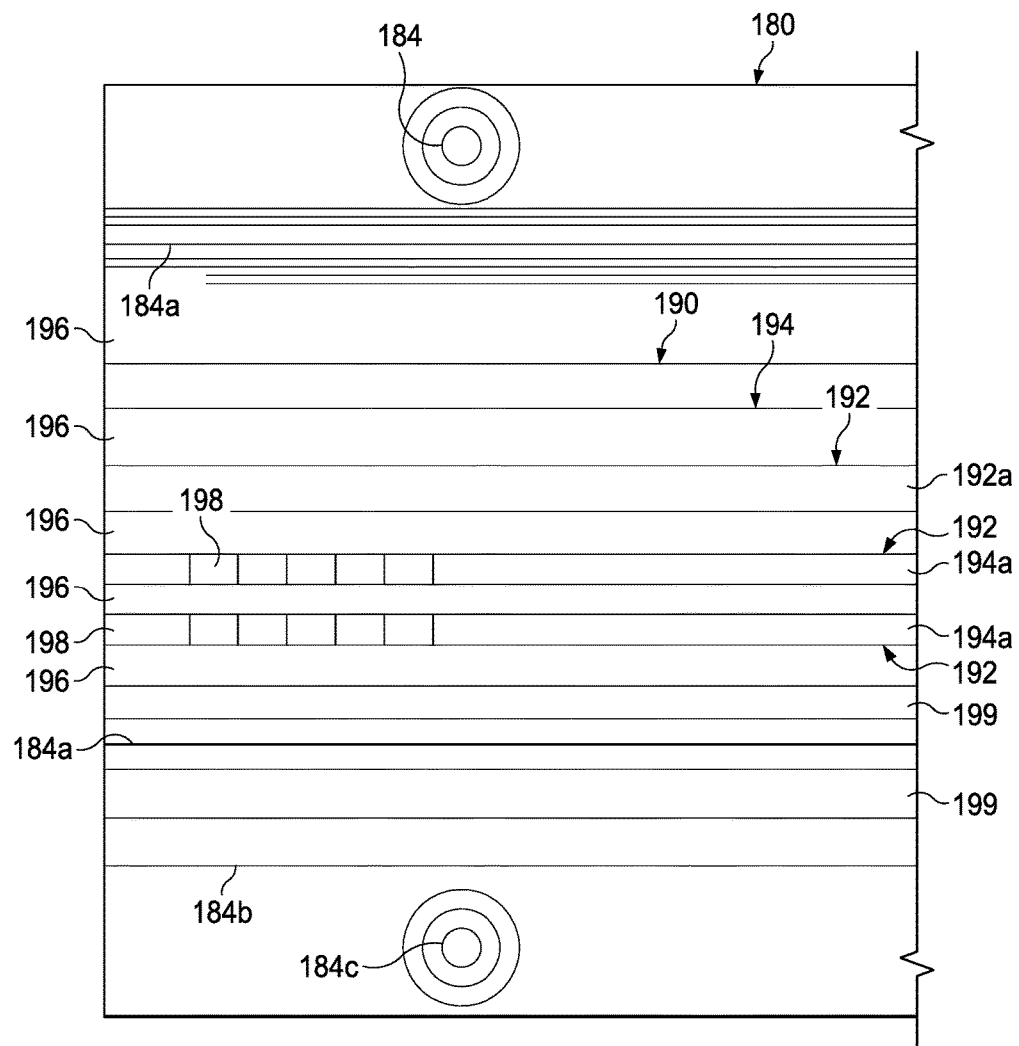
FIG. 5 is a top view of the film overlay in FIG. 4C, according to one example embodiment.

The internal structures 170 of the tail boom 160 are not apparent from the exterior, as shown in FIG. 4A. Accordingly, in an exemplary inspection method the film overlay 180 is positioned on the outer surfaces 162a and 164a of the side wall 162 and the top wall 164 to visually convey information about the tail boom 160 to the inspector as shown in FIGS. 4B and 4C.

The film overlay 180 includes at least one reference indicia 184a that visually conveys information about the location of a reference feature 140a on the tail boom 160. The inspector aligns the reference indicia 184a with the reference features 140a, which in this example are seams in the exterior surface 162a and 164a. In other examples, the reference features 140a can be at least one of an edge, a fastener, and a protruding component or surface. The reference feature 140a can be at least one of the following: an exterior feature of the component apparent to the operator, an internal structural feature of the component, and an internal non-structural feature of the component.

In another example, the reference indicia 184b is an image representing an internal structural component 140b that is an internal bracing member 170 not visually apparent to the operator. The operator can align the reference indicia 184b using non-destructive testing signals to locate the internal structural component 140b.

An embodiment provides that the reference feature 140c is an internal non- structural feature, for example, but not limitation a support fitting, an operating system, fasteners, or other internally located non-structural component. The exemplary reference features 140c indicate internal supports for an internal drive system. Non-destructive testing signals can be used to identify the internal non-structural reference features 140c to align the corresponding reference indicia 184c therewith. In an exemplary embodiment, the structural indicia 190 indicates the location of bonded hydraulic systems, wiring, or fasteners within the component.

Structural indicia 190 is included on the film overlay 180 to visually convey information about surfaces, materials, and the location of a structural feature within the tail boom 160 component. As shown in FIG. 4B, the structural indicia 190 can identify the primary structural components such as internal bracing members 170 on the exterior side surface 162a and top surface 164a as indicated by lines 192. The probe 150 is positioned on the top surface of the film overlay 180 and aligned with the lines 192. The structural indicia 190 further identifies bond lines 194.

In an embodiment, the structural indicia 190 is at least one image representing a structural feature or sub-structural feature. The structural or sub-structural feature can include one or more of the following: a first surface, a core, a second surface, a skin, multi-layer material stiffener, a composite layer, changing ply thickness, a co-bonded stiffener, a secondary adhesive bonded stiffener, a material layup, a hex-shaped honeycomb core, a cellular based core, a composite with unidirectional materials, a composite with bias materials, a composite with tri-axial materials, a material, a fiber direction, a ribbon direction, a ply thickness, a ply buildup, a ply drop-off, a mix of fibers, a tow angle, a bundle angle, a tow-size, a slit width, a tow separation, a bundle separation, a helical cell, an encapsulated material, internal variable members, an internal bracing member, a plurality of materials sandwiched together, a carbon epoxy sheet, a fiberglass sheet, a primary structural member, a secondary structural member, a substructure, a bondline, a septum, a web stiffener location indicating the location of an I-beam stiffener, and a partially corrugated septum. The structural indicia 190 can be an image representing an absence of a structural feature. The structural indicia 190 can be an image representing an individual structural feature or a plurality of structural features.

In one embodiment, the structural indicia 190 is at least one image representing a physical property of a structural feature. The physical property can be an indication of rigidity, thickness, material type, and alternate geometries.

In an embodiment, the structural indicia 190 is at least one image representing maintenance, service, installation, or other instructions related to a structural feature. For example, but not limitation, the structural indicia 190 can include a repair location and a repair type for a structural feature.

FIG. 4C is an exemplary embodiment of the structural indicia 190 identifying the primary structural components such as internal bracing members 170 as indicated in FIG. 4B and additional features. The structural indicia 190 further includes images representing multi-layer material stiffeners 192a, secondary adhesive bonded stiffeners 194a, skin surfaces 196, changing ply thickness 198, and co-bonded stiffener 199.

In one embodiment, at least one of the reference indicia 184a and structural indicia 190 is positioned on a top surface of the film overlay 180. In another embodiment, at least one of the reference indicia 184 and 190 is positioned on a bottom surface of the film overlay 180. In an embodiment, the film overlay is a polyimide film, or other suitable transparent film that does not interfere with the signal transmitted from the probe, can be contoured to the geometry of a component, can be moved or adjusted, and is at least in part transparent. In an embodiment, the film overlay 180 is a material that has the ability to transfer inspection energies without attenuating or reducing signal strength beyond 0.5 decibels at a frequency of 5.0 MHz. The reference indicia 184 and structural indicia 190 are imprinted, etched, or otherwise positioned or marked by a conventional printing device on a front surface 182a or back surface 182b of the film overlay 180.

Referring now also to FIGS. 6-12, an exemplary rotor blade 120 is illustrated. Rotor blade 120 has a root end 123 with a curved edge 126 and a tip end 125, which define a lengthwise axis therebetween. Rotor blade 120 also has a leading edge 122 and a trailing edge 124, which define a chordwise axis therebetween. It should be appreciated that rotor blade 120 is illustrative only and that alternative embodiments of rotor blade 120 can be configured in a variety of shapes and sizes.

Figure 7:
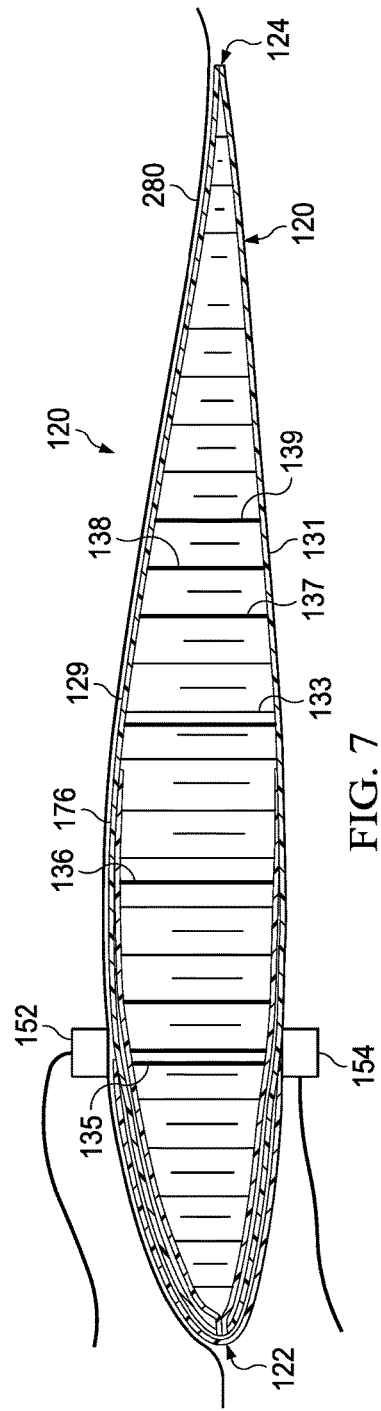
FIG. 7 is cross-sectional view of the rotor blade taken from section line 7-7 in FIG. 6 with an ultrasonic inspection system, according to one example embodiment.

Referring now also to FIG. 7, the rotor blade 120 can include a first surface 129, a second surface 131, core member 133, and an abrasion strip 135. The first surface 129 and second surface 131 can be an assembly of composite layers that are assembled and cured. The first surface 129 and the second surface 131 can have varying thicknesses and material layups which are implementation specific. Further, core member 133 is illustrated as a hex-shaped honeycomb core; however, the disclosure herein is not limited to a hex-shaped core, rather other core shapes can also be implemented. The core member 133 includes septums 135, 136, 137, 138, and 139 that add strength for carrying the tension of in-plane loading. The septums 135, 136, 137, 138, and 139 can be one or more plies of a composite material. The septum can be an enclosed septum that is encapsulated and adds strength around a plurality of cells.

The core member 133 can include structural features of composite unidirectional, bias, and tri-axial material. Moreover, the core member 133 can include structural features identified as a fibrous material having at least one of the following physical characteristics: tow-size or slit-width, tow or bundle separation, a tow angle, a bundle angle, hybrid mix of fibers, material ply thickness, and/or by ribbon direction or absence of ribbon direction. Further, the core member 133 can include a helical component of a core cell with any of the above variables, and can even include corrugated ply in a specific direction, between helical core cell components, or alternately incasing or encapsulating helical core cell components, individually or in groups. The core member 133 can include any combination of these variables to create directional stability (strength and/or stiffness), increase shear capability, and tailor the general properties of rotor blade 120 for a specific application or aircraft.

Figure 6:
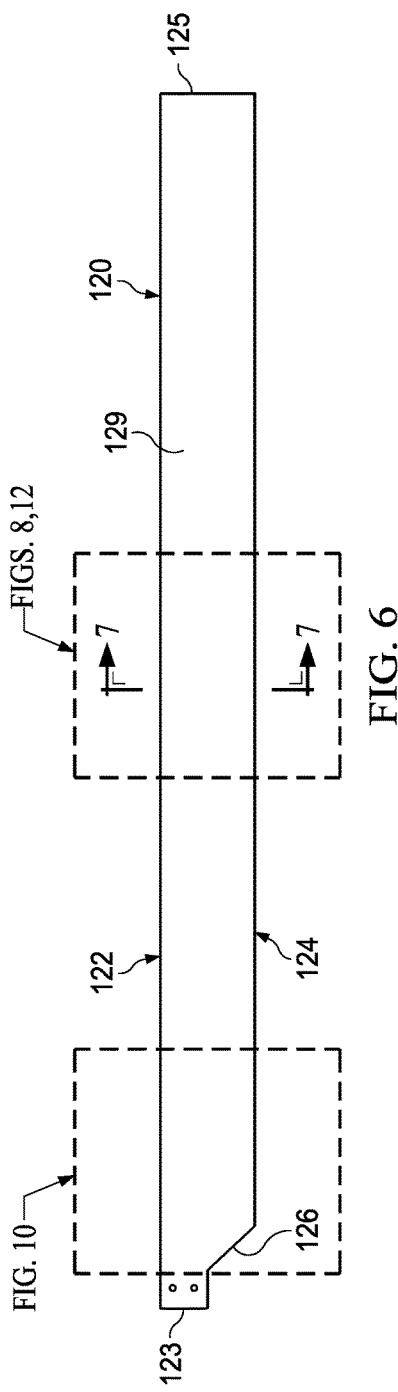
FIG. 6 is a top view of a rotor blade, according to one example embodiment.

The internal variable core structures are not readily apparent from the exterior, as show in FIG. 6. Accordingly, in an exemplary inspection method the film overlay 280 is positioned on the first surface 129 to visually convey information about the rotor blade 120 to the inspector as shown in FIGS. 7-9.

Figure 9:
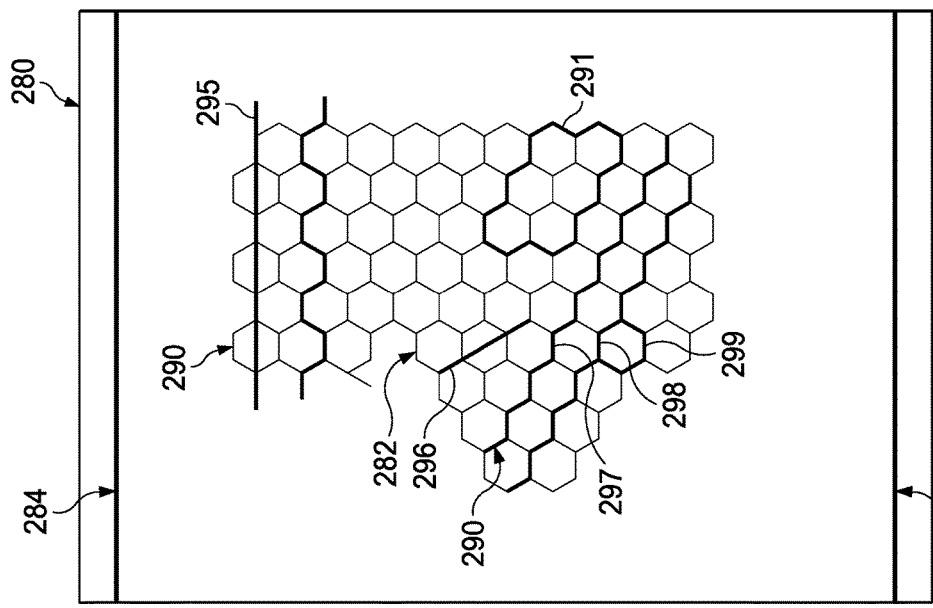
FIG. 9 is a top view of the film overlay in FIG. 8; according to an exemplary embodiment.
Figure 8:
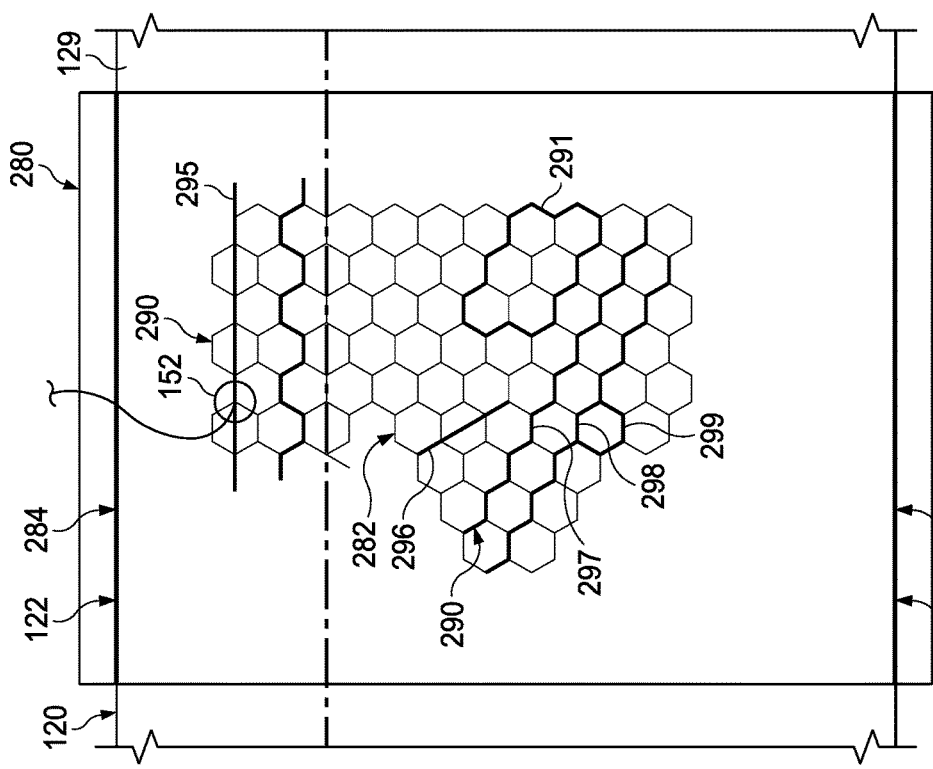
FIG. 8 is a top view of the rotor blade in FIG. 7 with a film overlay positioned on a top surface, according to one example embodiment.

The reference indicia 282 in FIGS. 7-9 is an image representing an internal structural cell of a honeycomb carbon core structure. The operator uses non-destructive testing data to locate the internal structural cell in the honeycomb structure and aligns the reference indicia 282 therewith to position the film overlay 280 on the rotor blade 120.

In some embodiments, the reference indicia lines 284 correspond to exterior features such as the leading edge 122 and the trailing edge 124 reference features of the rotor blade 120.

With the film overlay 280 in aligned position on the rotor blade 120, the structural indicia 290 corresponds to and otherwise represents the structural features in the rotor blade 120. For example, the structural indicia 290 indicates that the core member 133 is a hex-shaped honeycomb core by the hex-shaped imprinted lines on the film overlay 280. The structural indicia 295, 296, 297, 298, and 299 represent the septums 135, 136, 137, 138, and 139. The structural indicia 291 identifies an enclosed septum.

The inspector positions an ultrasonic transmitting probe 152 on the top surface of the film 280 and aligns the probe 152 with a structural indicia, for example, the structural indicia 295 shown as a septum line on the film overlay 280. An ultrasonic signal is transmitted from the probe 152 through the film overlay 280, a couplant 176, the first surface 129, the core 133 and the septum 135, and the second surface 133, The signal transmitted from the second surface 133 is the response signal that is received by the ultrasonic receiving probe 154. The inspector evaluates the response signal to identify any defects in the rotor blade 120.

FIGS. 10-11 is another embodiment of an exemplary inspection method using the film overlay 380 positioned on the first surface 129 near the root end 123 to visually convey information about the rotor blade 120 to the inspector.

The reference indicia 382 in FIGS. 10-11 is an image representing an internal structural cell of a honeycomb carbon core structure. The operator uses non-destructive testing data to locate the internal structural cell in the honeycomb structure and aligns the reference indicia 382 therewith to position the film overlay 380 on the rotor blade 120.

In some embodiments, the reference indicia lines 384 and 386 correspond to exterior features such as the leading edge 122, the trailing edge 124, and the curved edge 126 reference features of the rotor blade 120.

With the film overlay 380 in aligned position on the rotor blade 120, the structural indicia 390 corresponds to and otherwise represents the structural features in the rotor blade 120. For example, the structural indicia 390 indicates that the core member 133 is a double walled hex-shaped honeycomb core as indicated by the double walled hex-shaped imprinted lines on the film overlay 390. The structural indicia 391 identifies a partially corrugated septum by the lines 391 imprinted on the film overlay 380. The structural indicia 391A identifies the absence of a septum or other internal feature on the film overlay 380. The structural indicia 398 is a line representing a straight septum on the film overlay 380.

The inspector can position an ultrasonic transmitting probe 152 on the top surface of the film 380 and align the probe 152 with a structural indicia, such as the structural indicia 391 representing a partially corrugated septum.

Figure 12:
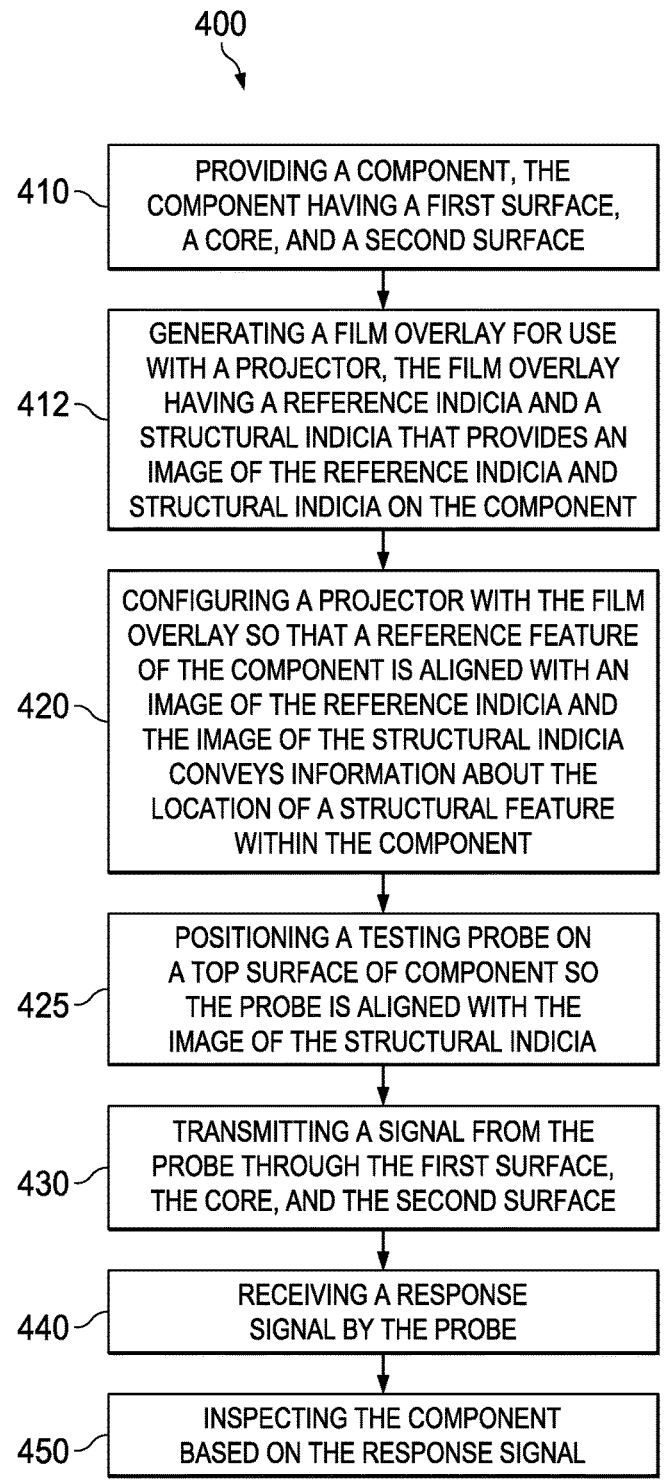
FIG. 12 shows a flowchart of an example inspection process for a component, according to one example embodiment.

Another embodiment of an inspection method 400 is shown in FIG. 12. The method 400 includes providing a component, the component having a first surface, a core, and a second surface 410. A film overlay is generated for use with a projector, the film overlay having a reference indicia and a structural indicia in step 412. The step 412 further includes positioning the film overlay near a light source in the projector to transmit an image of the reference indicia and the structural indicia.

The projector with the film overlay is positioned or otherwise configured to align the reference indicia image with a reference feature of the component 420. In another embodiment, the film overlay or the component is positioned to align the reference indicia image with an external or internal reference feature, which also aligns and provides an image of the structural indicia on the component in step 420. The image of the structural indicia conveys information about the location of a structural feature of the component. The inspector can position a testing probe on a top surface of component so the probe is aligned with the structural indicia 425 and transmits a signal from the probe through the first surface, the core, and the second surface 430. A response signal is received by the probe 440, which is then used to identify a defect when inspecting the component in step 450.

Figure 13:
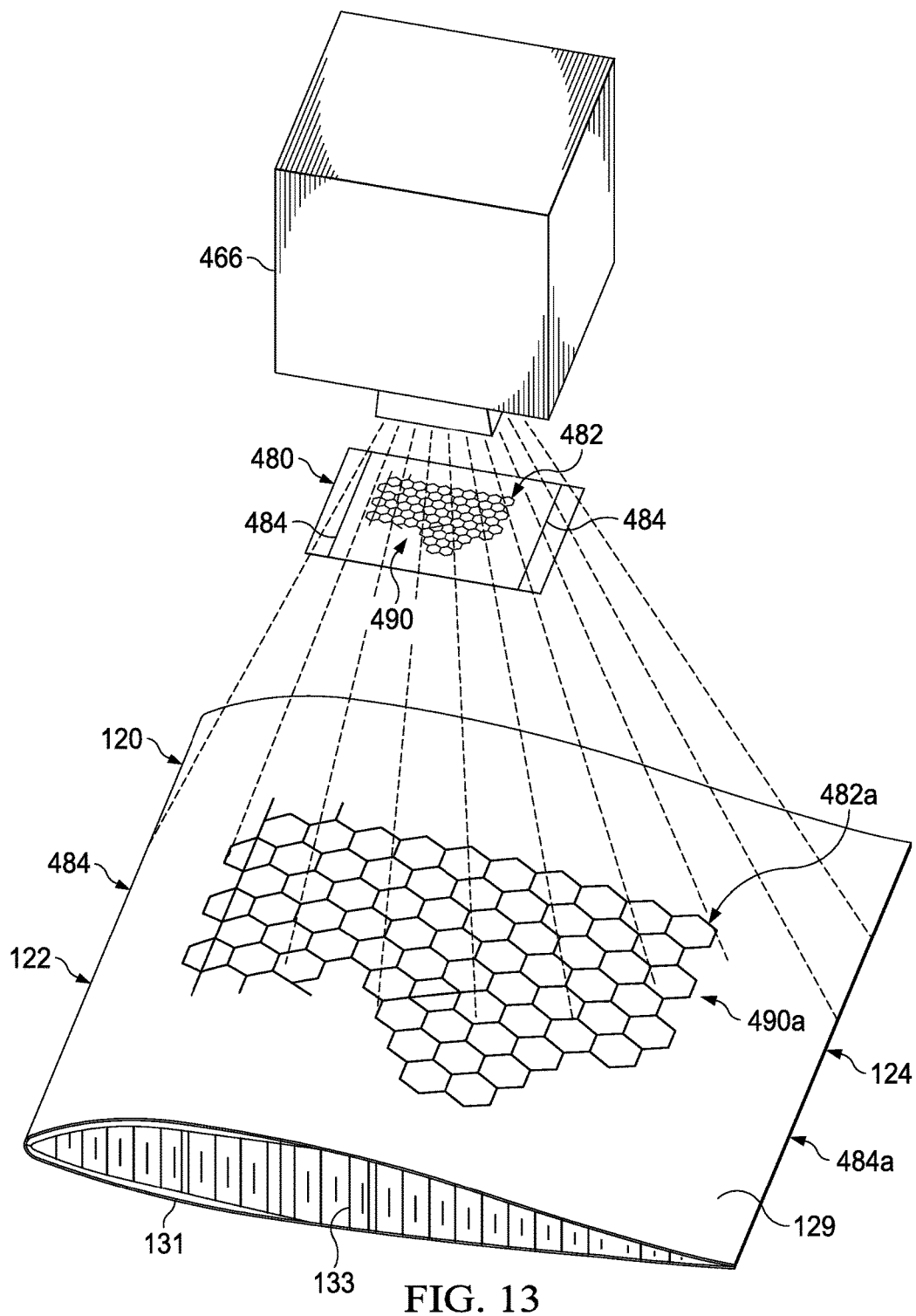
FIG. 13 is a schematic illustration of the film overlay being used with a projector to project an image of the reference indicia and structural indicia on the component, according to an exemplary embodiment.

FIG. 13 is an exemplary embodiment of the method 400 including a projector 466 with a light source that transmits light through the film overlay 480 having the reference indicia 482 and structural indicia 490 imprinted thereon. The projector 466 can be a conventional projector or a light emitting source such as a phone or other handheld device that emits light sufficient to transmit an image from the film overlay 480. The film overlay 480 is generally of a smaller size as compared to the film overlay used in the methods 200 and 300.

In one embodiment, the reference indicia 482 and structural indicia 490 imprinted on the film overlay 480 does not permit light to travel through the printed areas; thus, the image of the reference indicia 482a and the structural indicia 490a is shown as dark portions on the rotor blade 120, as shown in FIG. 13. In another embodiment, the film overlay itself is printed with a light blocking layer except in the reference indicia 482 and the structural indicia 490 areas; which shows the image of reference indicia 482a and the structural indicia 490a as lighted image against a dark background on the first surface 129 of the rotor blade 120.

In an embodiment, the reference indicia 482 represents an internal structural cell of a honeycomb core structure. The operator can use non-destructive testing data to locate the internal structural cell in the honeycomb structure and aligns the reference indicia 482 therewith.

In some embodiments, the reference indicia lines 484a correspond to exterior features such as the leading edge 122 and the trailing edge 124 of the rotor blade 120.

The illustrative embodiments of the inspection methods using a film overlay can advantageously be performed quickly since the inspector merely inspects along the structural indicia as opposed to testing large general areas that may have damage. The specific internal features of the component can be identified rapidly using the film overlay. The methods of inspection disclosed herein can be easily implemented in field operations to assess whether internal structures may be damaged.

At least one embodiment is disclosed and variations, combinations, and/or modifications of the embodiments) and/or features of the embodiment(s) made by a person having ordinary skill in the art within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes 2, 3, 4, etc.; greater than 0.10 includes 0.11, 0.12, 0.13, etc.). For example, whenever a numerical range with a lower limit, $R_l$, and an upper, $R_u$, is disclosed, any number falling within the range is specifically disclosed. In particular, the following numbers within the range are specifically disclosed: $R=R_l+k*(R_u-R_l)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Unless otherwise stated, the term "about" shall mean plus or minus 5 percent of the subsequent value. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having, should be understood to provide support for narrow terms such as consisting of, consisting essentially of, and comprised substantially of. Accordingly, the scope of protection is not limited by the description set out above but is defined by the claims that follow, the scope including all equivalents of the subject matter of the claims. Each and every claim is incorporated as further disclosure into the specification and the claims are embodiment(s) of the present invention.

The invention claimed is:

1. A method of inspecting a component, comprising:
   providing the component, the component having a first surface, a core, and a second surface;
   positioning a film overlay having a reference indicia and a structural indicia on the first surface of the component;
   aligning the reference indicia on the film overlay with a reference feature on the component;
   positioning a testing probe on a top surface of the film overlay so the probe is aligned with the structural indicia; and
   transmitting a signal from the probe through the film overlay, the first surface, the core, and the second surface.

2. The method of claim 1, further comprising:
   receiving a response signal by the probe; and
   inspecting the component based on the response signal.

3. The method of clam 1, wherein the reference indicia visually conveys information about the location of a reference feature on the component to identify the position of the film overlay on the component.

4. The method of claim 3, wherein the reference indicia is an image representing a reference feature selected from the group consisting of an exterior feature, an internal structural feature, and an internal non-structural feature.

5. The method of claim 1, wherein the structural indicia visually conveys information about the location of a structural feature within the component.

6. The method of claim 5, wherein the structural indicia is at least one image representing a structural feature selected from the group consisting of a first surface, a core, a second surface, a skin, multi-layer material stiffener, a composite layer, changing ply thickness, a co-bonded stiffener, a secondary adhesive bonded stiffener, a material layup, a hex-shaped honeycomb core, a cellular based core, a composite with unidirectional materials, a composite with bias materials, a composite with tri-axial materials, a material, a fiber direction, a ribbon direction, a ply thickness, a ply buildup, a ply drop-off, a mix of fibers, a tow angle, a bundle angle, a tow-size, a slit width, a tow separation, a bundle separation, a helical cell, an encapsulated material, internal variable members, an internal bracing member, a plurality of materials sandwiched together, a carbon epoxy sheet, a fiberglass sheet, a primary structural member, a secondary structural member, a substructure, a bondline, a septum, a web stiffener location indicating the location of an I-beam stiffener, and a partially corrugated septum.

7. The method of claim 1, wherein the film overlay is a polyimide film.

8. A film overlay for inspecting a component comprising:
   a transparent film sheet;
   a reference indicia positioned on the sheet; and
   a structural indicia positioned on the sheet;
   wherein the reference indicia visually conveys information about the location of a reference feature on the component to identify the position of the film overlay on the component; and
   wherein the structural indicia visually conveys information about the location of a structural feature within the component.

9. The film overlay of claim 8, wherein the film is a polyimide film.

10. The film overlay of claim 8, wherein the reference indicia is an image representing a reference feature selected from the group consisting of: an exterior feature, an internal structural feature, and an internal non-structural feature.

11. The film overlay of claim 8, wherein the structural indicia is at least one image representing a structural feature selected from the group consisting of a first surface, a core, a second surface, a skin, multi-layer material stiffener, a composite layer, changing ply thickness, a co-bonded stiffener, a secondary adhesive bonded stiffener, a material layup, a hex-shaped honeycomb core, a cellular based core, a composite with unidirectional materials, a composite with bias materials, a composite with tri-axial materials, a material, a fiber direction, a ribbon direction, a ply thickness, a ply buildup, a ply drop-off, a mix of fibers, a tow angle, a bundle angle, a tow-size, a slit width, a tow separation, a bundle separation, a helical cell, an encapsulated material, internal variable members, an internal bracing member, a plurality of materials sandwiched together, a carbon epoxy sheet, a fiberglass sheet, a primary structural member, a secondary structural member, a substructure, a bondline, a septum, a web stiffener location indicating the location of an I-beam stiffener, and a partially corrugated septum.

12. The film overlay of claim 8, wherein the structural indicia is at least one image representing the absence of the structural feature.

13. The film overlay of claim 8, wherein the structural indicia is at least one image representing an individual structural feature.

14. The film overlay of claim 8, wherein the structural indicia is at least one image representing a plurality of structural features.

15. The film overlay of claim 8, wherein the structural indicia is at least one image representing a physical property of the structural feature.

16. The film overlay of claim 8, the structural indicia is selected from the group consisting of maintenance instructions, service instructions, and installation instructions.

17. A method of inspecting a component, comprising:
   providing the component, the component having a first surface, a core, and a second surface;
   generating a film overlay for use with a projector, the film overlay having a reference indicia and a structural indicia that provides an image of the reference indicia and structural indicia on the component; and
   configuring a projector with the film overlay so that a reference feature of the component is aligned with an image of the reference indicia and the image of the structural indicia conveys information about the location of a structural feature within the component.

18. The method of claim 17, further comprising:
positioning a testing probe on a top surface of component so the probe is aligned with the image of the structural indicia; and
transmitting a signal from the probe through the first surface the core, and the second surface.

19. The method of claim 18, further comprising:
receiving a response signal by the probe; and
inspecting the component based on the response signal.

* * * * *

UNITED STATES PATENT AND TRADEMARK OFFICE
CERTIFICATE OF CORRECTION

PATENT NO. : 9,939,391 B1  
APPLICATION NO. : 15/380408  
DATED : April 10, 2018  
INVENTOR(S) : Edward A. Hohman Page 1 of 1

It is certified that error appears in the above-identified patent and that said Letters Patent is hereby corrected as shown below:

In the Specification

Column 7, Line 2, "140cto" should be -140c to-

Column 10, Line 50, "embodiments)" should be -embodiment(s)-

In the Claims

Column 13, Claim 18, Line 6, "surface the core" should be -surface, the core-

Signed and Sealed this
Tenth Day of July, 2018

Andrei Iancu
*Director of the United States Patent and Trademark Office*